United States Patent
Konieczynski et al.

(10) Patent No.: US 9,155,569 B2
(45) Date of Patent: Oct. 13, 2015

(54) LAMINOPLASTY METHODS USING HINGE DEVICE

(71) Applicant: DePuy Spine, Inc., Raynham, MA (US)

(72) Inventors: David D. Konieczynski, Needham, MA (US); John R. Hawkins, Cumberland, RI (US); Michael A. Slivka, Taunton, MA (US); Edward B. Zalenski, Lakeville, MA (US); Jayson S. Page, Attleboro, MA (US); Michael Mazzuca, North Easton, MA (US); Michael Jacene, Blackstone, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 225 days.

(21) Appl. No.: 13/860,930

(22) Filed: Apr. 11, 2013

(65) Prior Publication Data

US 2013/0226249 A1    Aug. 29, 2013

Related U.S. Application Data

(62) Division of application No. 12/406,726, filed on Mar. 18, 2009, now Pat. No. 8,435,265.

(51) Int. Cl.
*A61B 17/88* (2006.01)
*A61B 17/70* (2006.01)
(Continued)

(52) U.S. Cl.
CPC .......... *A61B 17/7059* (2013.01); *A61B 17/7071* (2013.01); *A61B 17/808* (2013.01); *A61B 17/863* (2013.01); *A61B 17/866* (2013.01); *A61B 2017/8655* (2013.01); *A61B 2019/307* (2013.01)

(58) Field of Classification Search
CPC ........... A61B 17/7071; A61B 17/7059; A61B 17/7065; A61B 17/808; A61B 17/7044; A61B 17/7062–17/7067; A61B 17/707
See application file for complete search history.

(56) References Cited

U.S. PATENT DOCUMENTS 2,580,821 A    1/1952  Toufick
4,905,679 A    3/1990  Morgan
(Continued)

FOREIGN PATENT DOCUMENTS

WO    03/101319 A2    12/2003

OTHER PUBLICATIONS

Int. Search Report PCT/US2010/024698, Apr. 23, 2010.
(Continued)

*Primary Examiner* — Eduardo C Robert
*Assistant Examiner* — Jacqueline Johanas
(74) *Attorney, Agent, or Firm* — Nutter McClennen & Fish LLP

(57) ABSTRACT

A vertebra implant is provided that includes an elongate body with a first end configured to mate the first end to a first location on a vertebra, and a second end having at least one fastener configured to mate the second end to a second location on a vertebra. The elongate body also includes a deformable portion extending between the first and second ends that has an unexpanded configuration in which the deformable portion is configured to allow a tool to cut bone extending between the first and second ends when the first and second ends are mated to first and second locations on a vertebra, and an expanded configuration in which the deformable portion is deformed to increase a distance between the first and second ends such that a gap is created in the cut bone. The deformable portion is configured to maintain the first and second ends at a fixed distance apart when the deformable portion is in the expanded configuration. A vertebral implant is also provided that includes an elongate member configured to extend into a vertebra and form a hinge therein using a breakage point located along a length of the elongate member.

15 Claims, 13 Drawing Sheets

(51) Int. Cl.
  *A61B 17/80*  (2006.01)
  *A61B 17/86*  (2006.01)
  *A61B 19/00*  (2006.01)

(56) References Cited

U.S. PATENT DOCUMENTS

| | | | |
|---|---|---|---|
| 5,176,679 A | 1/1993 | Lin | |
| 5,415,661 A | 5/1995 | Holmes | |
| 5,468,242 A | 11/1995 | Reisberg | |
| 5,752,958 A | 5/1998 | Wellisz | |
| 5,827,286 A | 10/1998 | Incavo et al. | |
| 5,984,925 A | 11/1999 | Apgar | |
| 6,080,157 A | 6/2000 | Cathro et al. | |
| 6,093,188 A | 7/2000 | Murray | |
| 6,358,254 B1 | 3/2002 | Anderson | |
| 6,364,881 B1 | 4/2002 | Apgar et al. | |
| 6,635,087 B2 * | 10/2003 | Angelucci et al. | 623/17.11 |
| 6,712,852 B1 | 3/2004 | Chung et al. | |
| 6,761,719 B2 | 7/2004 | Justis et al. | |
| 7,090,676 B2 | 8/2006 | Huebner et al. | |
| 7,166,107 B2 | 1/2007 | Anderson | |
| 7,189,237 B2 | 3/2007 | Huebner | |
| 7,264,620 B2 | 9/2007 | Taylor | |
| 7,297,146 B2 * | 11/2007 | Braun et al. | 606/279 |
| 7,799,061 B2 | 9/2010 | Kay et al. | |
| 8,105,366 B2 | 1/2012 | Null et al. | |
| 8,118,846 B2 | 2/2012 | Leither et al. | |
| 8,147,528 B2 | 4/2012 | Mazzuca et al. | |
| 8,162,996 B2 | 4/2012 | Schelling | |
| 8,231,663 B2 | 7/2012 | Kay et al. | |
| 8,246,682 B2 * | 8/2012 | Slivka et al. | 623/17.11 |
| 8,435,265 B2 * | 5/2013 | Konieczynski et al. | 606/246 |
| 8,894,714 B2 * | 11/2014 | Makower et al. | 623/20.21 |
| 8,926,664 B1 * | 1/2015 | Millhouse et al. | 606/246 |
| 2002/0004660 A1 | 1/2002 | Henniges et al. | |
| 2003/0045935 A1 | 3/2003 | Angelucci et al. | |
| 2003/0233093 A1 | 12/2003 | Moles et al. | |
| 2004/0002708 A1 | 1/2004 | Ritland | |
| 2004/0030388 A1 | 2/2004 | Null et al. | |
| 2004/0064140 A1 | 4/2004 | Taylor et al. | |
| 2004/0102776 A1 | 5/2004 | Huebner | |
| 2004/0107003 A1 | 6/2004 | Boyer et al. | |
| 2004/0172040 A1 | 9/2004 | Heggeness | |
| 2005/0119657 A1 | 6/2005 | Goldsmith | |
| 2005/0149030 A1 * | 7/2005 | Serhan et al. | 606/73 |
| 2005/0171539 A1 | 8/2005 | Braun et al. | |
| 2005/0182408 A1 | 8/2005 | Pfefferle et al. | |
| 2005/0273100 A1 | 12/2005 | Taylor | |
| 2005/0273104 A1 | 12/2005 | Oepen et al. | |
| 2006/0036259 A1 | 2/2006 | Carl et al. | |
| 2006/0058796 A1 | 3/2006 | Hartdegen et al. | |
| 2006/0084985 A1 | 4/2006 | Kim | |
| 2006/0089645 A1 | 4/2006 | Eckman | |
| 2006/0122607 A1 | 6/2006 | Kolb | |
| 2006/0200145 A1 | 9/2006 | Kay et al. | |
| 2006/0235408 A1 | 10/2006 | Wang et al. | |
| 2007/0049937 A1 | 3/2007 | Matthis et al. | |
| 2007/0055236 A1 | 3/2007 | Hudgins et al. | |
| 2007/0073405 A1 | 3/2007 | Verhulst et al. | |
| 2007/0191837 A1 | 8/2007 | Trieu | |
| 2007/0213828 A1 | 9/2007 | Trieu et al. | |
| 2007/0219634 A1 | 9/2007 | Greenhalgh et al. | |
| 2008/0009865 A1 | 1/2008 | Taylor | |
| 2009/0210012 A1 | 8/2009 | Null et al. | |
| 2010/0036430 A1 | 2/2010 | Hartdegen et al. | |
| 2010/0057127 A1 | 3/2010 | McGuire et al. | |
| 2010/0063590 A1 * | 3/2010 | Cannestra | 623/17.11 |
| 2010/0121381 A1 * | 5/2010 | Berta et al. | 606/264 |
| 2010/0145386 A1 * | 6/2010 | Greenhalgh et al. | 606/246 |
| 2010/0152854 A1 * | 6/2010 | Slivka et al. | 623/17.12 |
| 2010/0241165 A1 | 9/2010 | Konieczynski et al. | |
| 2010/0241230 A1 | 9/2010 | Mazzuca et al. | |
| 2012/0143339 A1 * | 6/2012 | Voellmicke et al. | 623/17.16 |
| 2012/0165942 A1 * | 6/2012 | Khanna | 623/17.16 |
| 2012/0209338 A1 * | 8/2012 | Groiso | 606/331 |
| 2013/0238094 A1 * | 9/2013 | Voellmicke et al. | 623/17.11 |

OTHER PUBLICATIONS

Intl. Search Report PCT/US2010/024705, Apr. 23, 2010.

* cited by examiner

LAMINOPLASTY METHODS USING HINGE DEVICE

CROSS REFERENCE TO RELATED APPLICATIONS

This application is a divisional of U.S. application Ser. No. 12/406,726, filed on Mar. 18, 2009 entitled "Laminoplasty Methods Using Hinge Device" which is hereby incorporated by reference in its entirety.

FIELD OF THE INVENTION

The present invention relates methods and devices for increasing the size of a spinal canal.

BACKGROUND OF THE INVENTION

In certain pathologies, the spinal canal extending through a patient's vertebrae is or becomes too narrow and constricts the spinal cord extending therethrough. The narrowing may be congenital, potentially affecting patients at any age. Narrowing can also be attributable to other causes, such as age, injury or removal of a spinal disc.

A condition associated with aging, for instance, is spondylolisis, in which intervertebral discs loose water and become less dense. These degenerative changes near the disc can cause an overgrowth of the bone, producing bony spurs called "osteophytes" that can compress the spinal cord. The constriction of the spinal cord in the cervical spine, for example, often produces pain, weakness, or loss of feeling in extremities. Other causes for narrowing of the spinal canal include disc shrinkage, which causes the disc space to narrow and the annulus to bulge and mushroom out, resulting in pressure on the spinal cord. Degenerative arthritis of facet joints can cause joints to enlarge, or the vertebra to slip with respect to each other, also compressing the spinal cord. Instability between vertebra, such as caused by stretched and thickened ligaments' can also produce pressure on the spinal cord and nerve roots.

Myelopathy, or malfunction of the spinal cord, occurs due to its compression. The rubbing of the spine against the cord can also contribute to this condition, and the spinal cord compression can ultimately compromise the blood vessels feeding the spinal core, further aggravating the myelopathy.

Traditional procedures for decompressing the spinal cord include a laminectomy, in which the lamina and spinal processes are removed to expose the dura covering the spinal cord. Another known procedure is a laminoplasty, in which the lamina is lifted off the dura, but not completely removed. Typically, one side of the lamina is cut, while a partial cut is made on the other side to hinge the lamina away from the spinal cord to increase the size of the spinal canal. A laminoplasty plate is then screwed to a lateral vertebral bone mass and to the hinged open lamina. A strut of bone can be placed in the open portion within the lamina and the lateral mass to help hold the open position of the lamina. Prior to the operation, the surgeon needs to measure the vertebra to determine the size of the plate necessary for implantation. At that point, a plate can be selected with the appropriate dimensions, and implanted at the site. There can be difficulty in the determination of the appropriate plate as the measurements must have sufficient accuracy as to make the correct plate selection.

Accordingly, there is a need for improved methods and devices for increasing the size of a spinal canal.

SUMMARY OF THE INVENTION

The present invention provides various devices and methods for increasing the size of a spinal canal. In one embodiment, a laminoplasty implant is provided and includes an elongate body with a first end having at least one fastener configured to mate the first end to a first location on a vertebra, and a second end having at least one fastener configured to mate the second end to a second location on a vertebra. The elongate body also includes a deformable portion extending between the first and second ends. The deformable portion has an unexpanded configuration in which the first and second ends of the implant can be mated to first and second locations on a vertebra prior to cutting the vertebra between the first and second locations, and an expanded configuration in which the deformable portion is deformed to increase a distance between the first and second ends such that a gap is created in the cut bone. In one embodiment, the deformable portion can be configured to allow a tool to cut bone extending between the first and second ends when the first and second ends are mated to bone. The deformable portion is configured to maintain the first and second ends at a fixed distance apart when the deformable portion is in the expanded configuration.

The fastener can have various configurations to mate the first and second ends to the vertebra. In one exemplary embodiment, the fastener on at least one of the first and second ends is disposed within a thru-hole formed in the elongate body, and the fastener can be, for example, a bone screw. In another exemplary embodiment, the fastener on at least one of the first and second ends can be a clamp formed on the elongate body and configured to engage bone.

The deformable portion can also have various configurations. In one exemplary embodiment, the deformable portion extends out of an axis extending between the first and second ends of the elongate body to allow a tool to cut bone positioned between the first and second ends of the elongate body. In other exemplary embodiments, the deformable portion can have at least one u-shaped region, can be in the form of an elongate coiled member, or can have a mesh configuration. The deformable portion can also have at least one bend formed therein in the unexpanded configuration, and it can be substantially linear in the expanded configuration.

The elongate body of the implant can also include a first feature, such as a cut-out, formed between the first end and the deformable portion and a second feature, such as a cut-out, formed between the second end and the deformable portion. The first and second features can face one another such that a tool having first and second jaws that pivot relative to one another can be positioned in the first and second features to apply a force to the first and second ends to move the deformable portion to the expanded configuration.

Methods for increasing a size of a spinal canal are also provided, and in one embodiment the method can include coupling a first end of an implant to a first location on a vertebra, coupling a second end of the implant to a second location on the vertebra, and cutting the vertebra between the first and second locations. A deformable portion of the implant can be deformed to increase and maintain a distance between the first and second locations on the vertebra thereby increasing a size of a spinal canal extending through the vertebra. Deforming the deformable portion of the implant can include inserting a tool between the first and second ends of the implant and actuating the tool to apply a force to the first and second ends of the implant to increase a distance therebetween. Deforming the deformable portion of the implant can also include stretching out at least one bend formed in the deformable portion.

In one exemplary embodiment, the vertebra is cut after coupling at least one of the first and second ends of the implant to the first and second locations on the vertebra. The first and second ends can be coupled to the vertebra in a variety of ways. For example, coupling at least one of the first and second ends of the implant to the first and second locations on the vertebra can include inserting a fastener through a thru-hole formed in the implant and inserting the fastener into the vertebra. In one exemplary embodiment, the first and second locations are on a lamina located on a first side of a spinous process of the vertebra, and cutting the vertebra can include separating the lamina into two portions. The method can also include forming a hinge in a lamina located on a second side of the spinous process of the vertebra.

The present invention also provides a laminoplasty implant kit that includes an elongate member configured to extend into a lamina on a first lateral side of a vertebra. The elongate member has a breakage point located along a length thereof that is configured to form a hinge in the lamina when the elongate member is disposed therein. The kit also includes an implant having first and second ends configured to mate to first and second locations on a lamina on a second lateral side of a vertebra. The first and second ends are configured to maintain the first and second locations on the lamina at a fixed distance apart from one another to thereby increase a size of a spinal canal extending through the vertebra. The implant can include an expandable portion located between the first and second ends and configured to expand to maintain the first and second locations on the lamina at a fixed distance apart from one another. The kit can also optionally include at least one fastener for mating the implant to bone.

The breakage point on the elongate member can have a variety of configurations. In one exemplary embodiment, the breakage point is in the form of a flexible region formed on the elongate member. In another exemplary embodiment, the breakage point is a hinge formed on the elongate member. In yet another exemplary embodiment, the breakage point is a probe disposed within the elongate member and movable between a first position in which a distal end of the probe is fully disposed within the elongate member, and a second position in which the distal end of the probe protrudes from an opening formed in a sidewall of the elongate member to penetrate bone and cause the lamina to break and form a hinge. The elongate member can be cannulated to allow for the probe to be inserted therein. In yet another exemplary embodiment, the breakage point is in the form of a weakened region formed on the elongate member and configured to break and form the hinge in the first lateral side of the vertebra.

Methods for increasing a size of a spinal canal are also provided, and in one embodiment the method can include implanting an elongate member in a lamina on first lateral side of a vertebra and applying a force to the elongate member to create a hinge in the lamina. The method also includes forming a cut in a lamina on a second lateral side of the vertebra to separate the lamina into two halves, and increasing a distance between the two halves of the lamina to expand a size of a spinal canal extending through the vertebra. The hinge pivots as the distance between the two halves of the lamina is increased. In one exemplary embodiment, the method can include coupling an implant to opposed sides of the cut in the lamina on the second lateral side of the vertebra. The distance between the two halves of the lamina can be increased by deforming a deformable portion on the implant to increase a length of the implant.

Force can be applied to the elongate member to create the hinge in a variety of ways. In one exemplary embodiment, applying a force to the elongate member includes inserting a tool into the elongate member to push a probe out of an opening formed in the sidewall of the elongate member. The probe can penetrate into the lamina to create the hinge. In another exemplary embodiment, applying a force to the elongate member causes a breakage point on the elongate member to break to create the hinge in the lamina. In yet another exemplary embodiment, applying a force to the elongate member causes a portion of the lamina adjacent to a distal tip of the elongate member to break to create the hinge in the lamina.

Methods for increasing the size of a spinal canal are provided, and in another embodiment the method can include accessing a first lateral side of the spine through an access port formed through tissue on the first lateral side of the spine, and forming a hinge on a second lateral side of the spine through the access port. The method also includes forming a cut in a lamina on the first lateral side through the access port to separate the lamina into two halves, and increasing a distance between the two halves of the lamina to expand a size of a spinal canal extending through the spine. The hinge pivots as the distance between the two halves of the lamina is increased.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides various methods and devices for increasing the size of a spinal canal. In general, a vertebral implant is provided that is adapted to couple to first and second locations on a vertebra, and that is adapted to expand to increase and maintain a distance between the first and second locations in order to increase the size of the spinal canal of the vertebra. The use of an expandable implant is particularly advantageous as it allows for in-situ adjustment of a distance between the two cut portions of a vertebra, thus allowing the distance to be set as desired without the need to measure and/or select an implant having a particular size. The present invention also provides methods and device for forming a hinge in a vertebra.

Figure 1A:
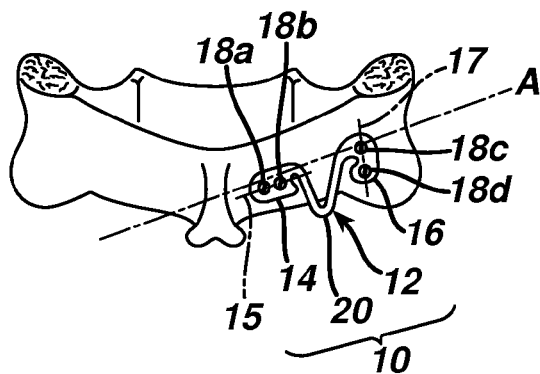
FIG. 1A is a perspective view of a vertebra having a vertebral implant coupled to first and second locations thereon, the implant having an elongate body with a deformable portion for increasing the size of a spinal canal of a vertebra.
Figure 1B:
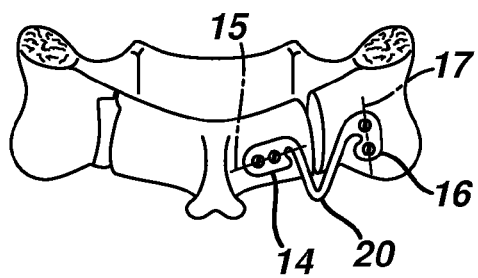
FIG. 1B is a perspective view of the vertebra and vertebral implant of FIG. 1A showing a cut formed between the first and second locations.
Figure 1C:
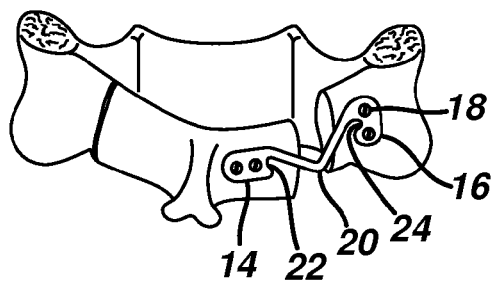
FIG. 1C is a perspective view of the vertebra and vertebral implant of FIG. 1B showing the deformable portion of the implant expanded to increase the size of a spinal canal of the vertebra.

FIGS. 1A-1C illustrate one exemplary embodiment of a vertebral implant 10 that is in the form of an elongate body having a first end 14 configured to coupled to a first location on a vertebra, and a second end 16 configured to coupled to a second location on a vertebra. A deformable portion 12 is formed between the first and second ends 14, 16, and it can be deformed between an unexpanded configuration in which the deformable portion 12 is preferably configured to allow a tool to cut bone between the first and second ends 14, 16 without interference from the deformable portion 12, and an expanded configuration in which the deformable portion 12 maintains a fixed distance between the first and second ends 14, 16. Movement from the unexpanded configuration to the expanded configuration allows the first and second locations on the vertebra to be moved apart to increase the size of a spinal canal of the vertebra.

The deformable portion 12 can be formed from a variety of materials that allow the deformable portion 12 to deform between the unexpanded and expanded configurations while also allowing the deformable portion 12 to maintain its deformed shape in the expanded configuration to maintain the distance between the first and second ends 14, 16 and increase the size of the spinal canal. Preferably, the deformable portion 12 is formed from a material that is deformable but not an elastic material, as it is necessary for the deformable portion 12 to maintain its expanded shape in the expanded configuration. For example, the deformable portion 12 can be formed from titanium, nitinol, stainless steel, or PEEK.

The deformable portion 12 can have a variety of configurations. In the embodiment shown in FIGS. 1A-1C, the deformable portion 12 is in the form of an elongate plate or rod that extends between the first and second ends 14, 16. The particular shape of the deformable portion 12 can vary, but in the illustrated embodiment the deformable portion 12 is V-shaped in its unexpanded configuration such that it extends out of an axis A extending between the first and second ends 14, 16. The V-shape can be formed by a bend 20 in the deformable portion 12. The bend 20 can have an angle, but is preferably 40° or less in the unexpanded configuration. This allows the first and second ends 14, 16 to be attached to bone at two locations that are very close to one another, i.e., immediately adjacent to a cut formed or to be formed in the bone. In use, the V-shape allows a tool to be passed through the deformable portion 12 so the bone positioned and extending between the first and second ends 14, 16 can be cut without interference from the deformable portion 12. In the expanded configuration, the deformable portion 12 can be stretched out to increase the angle of the bend 20 and, optionally, to make the deformable portion 20 more linear (although a slight bend can remain), as shown in FIG. 1C. While not shown, the implant 10 can also have various shapes to facilitate positioning against bone. For example, the entire implant can be planar, such that the first and second ends 14, 16 and the deformable portion 12 all lie in the same plane, or it can have a curved profile such that the first and second ends 14, 16 are oriented at a slight angle to one another to accommodate a curvature of the bone to which the implant is to be attached to.

Figure 2A:
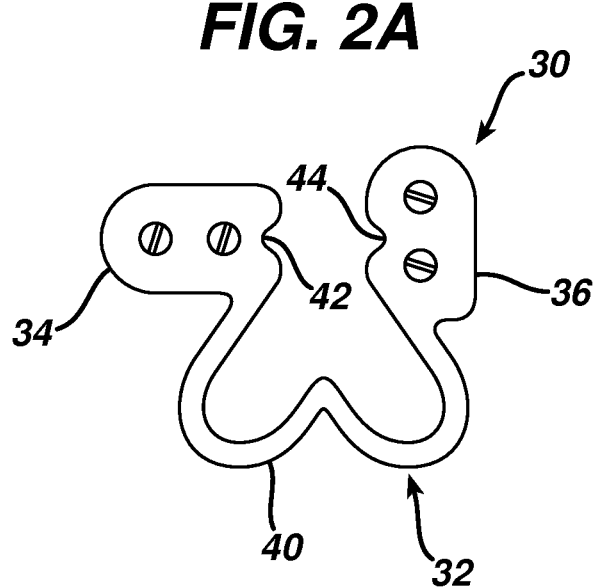
FIG. 2A is a top view of another embodiment of a vertebral implant having an elongate body with a deformable portion for increasing the size of a spinal canal of a vertebra.
Figure 2B:
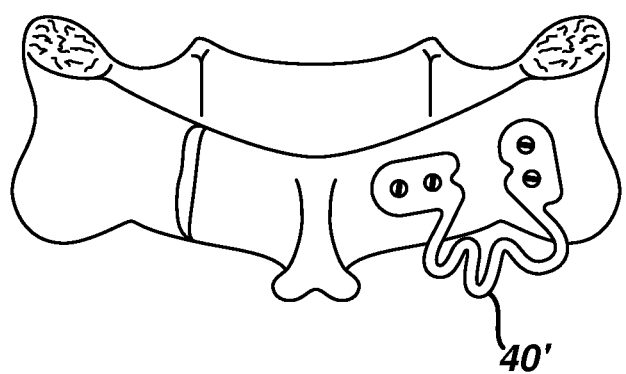
FIG. 2B is a perspective view of a vertebra having another embodiment of a vertebral implant coupled to first and second locations thereon showing a deformable portion of the implant shown in an unexpanded configuration.

A person skilled in the art will appreciate that the deformable portion 12 can have any number of bends 20 formed therein to vary the length and/or configuration of the deformable portion 12 depending on the desired increased in the distance between the first and second locations of the vertebra. For example, FIGS. 2A-2B illustrate additional embodiments of the deformable portion having multiple bends. FIG. 2A illustrates a vertebral implant 30 that has an elongate configuration with a first end 34 configured to be coupled to a first location on a vertebra, and a second end 36 configured to be coupled to a second location on a vertebra. A deformable portion 32 is formed between the first and second ends 34, 36, and it has a plurality of curved bends 40 formed along the length of the deformable portion 32. While the deformable portion 32 can have any number of curved bends 40, the deformable portion 32 shown includes two curved bends 40 such that it has a W-shape. In another embodiment shown in FIG. 2B, the deformable portion 32' includes three curved bends 40'. In use, the bends 40, 40' allow a tool to be passed through the deformable portion 32, 32' so the bone positioned and extending between the first and second ends can be cut without interference from the deformable portion 32, 32'. The curved bends of the deformable portions 32, 32' can be stretched out in the expanded configuration to increase the distance between the first and second ends 34, 36, thereby increasing the size of the spinal canal.

Figure 3A:
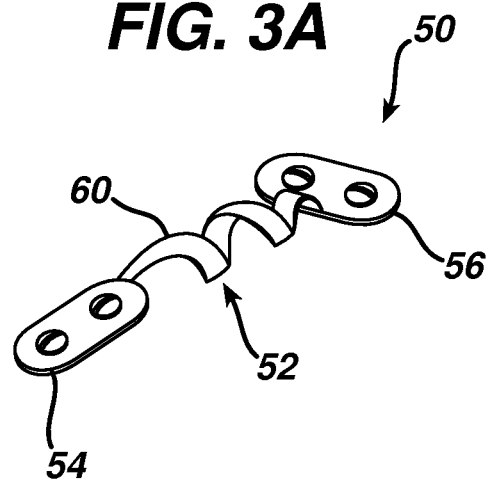
FIG. 3A is a perspective view of another embodiment of a vertebral implant having an elongate body with a deformable portion for increasing the size of a spinal canal of a vertebra.
Figure 3B:
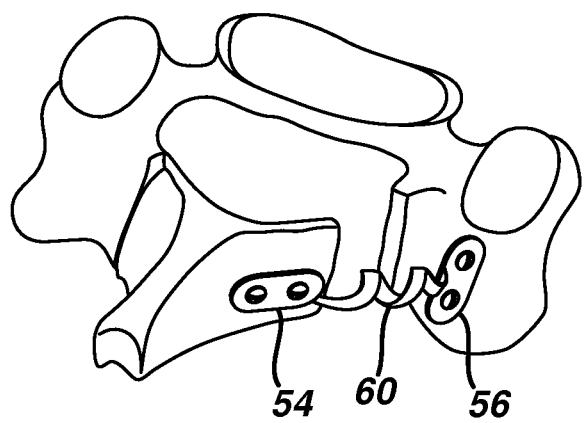
FIG. 3B is a perspective view of a vertebra having the vertebral implant of FIG. 3A coupled to first and second locations thereon showing the deformable portion of the implant expanded to increase the size of a spinal canal of the vertebra.

Various other configurations of a deformable portion of a vertebral implant can be used to increase the distance between first and second locations on a vertebra to increase the size of a spinal canal of the vertebra. In another exemplary embodiment, shown in FIGS. 3A-3B, a vertebral implant 50 is provided that has a generally elongate configuration with a first end 54 configured to be coupled to a first location on a vertebra, and a second end 56 configured to be coupled to a second location on a vertebra. A deformable portion 52 is formed between the first and second ends 54, 56 and it is in the form of a coiled member 60 that is coiled in the unexpanded configuration, as shown in FIG. 3A, and that can stretch out or partially uncoil in the expanded configuration, as shown in FIG. 3B. The size and length of the coil can vary depending on the desired increase in the size of the spinal canal of the vertebra. In use, the coil of the deformable portion 52 allows a tool to be passed through the deformable portion 12 so the bone positioned between the first and second ends 54, 56 can be cut without interference from the deformable portion 12 as the tool can be passed through the openings of the coil, or the coil can be deformed out of the way of the tool to allow the tool to cut bone.

Figure 4:
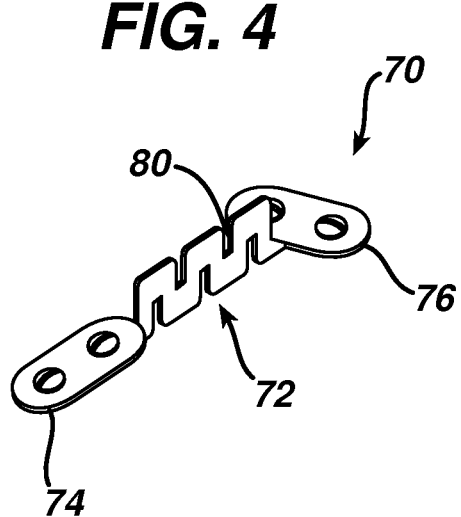
FIG. 4 is a perspective view of another embodiment of a vertebral implant having an elongate body with a deformable portion for increasing the size of a spinal canal of a vertebra.

In yet another exemplary embodiment, shown in FIG. 4, a vertebral implant 70 is provided that has an elongate configuration with a first end 74 configured to be coupled to a first location on a vertebra, and a second end 76 configured to be coupled to a second location on a vertebra. A deformable portion 72 is formed between the first and second ends 74, 76 and it is in the form of an elongate plate having a plurality of cut-outs 80 formed therein that allow the plate to expand laterally. In the illustrated embodiment, the deformable portion 72 resides in a plane that is perpendicular to a plane containing the first and second ends 74, 76. The cut-outs 80 are formed in each side of the deformable portion 72 in an alternating manner to form a zig-zag type pattern. While the illustrated embodiment shows the deformable portion 72 having five cut-outs 80, a person skilled in the art will appreciate that the deformable portion 72 can have any number of cut-outs 80 depending on the desired increase in the spinal canal of the vertebra. In use, the cut-outs 80 allow a tool to be passed through the deformable portion 72 so the bone positioned and extending between the first and second ends 74, 76 can be cut without interference from the deformable portion 12. For example, the tool can be passed through any of the cut-outs 80 to allow the tool to cut bone, or the deformable portion 72 can be deformed out of the way of the tool during cutting.

Figure 5A:
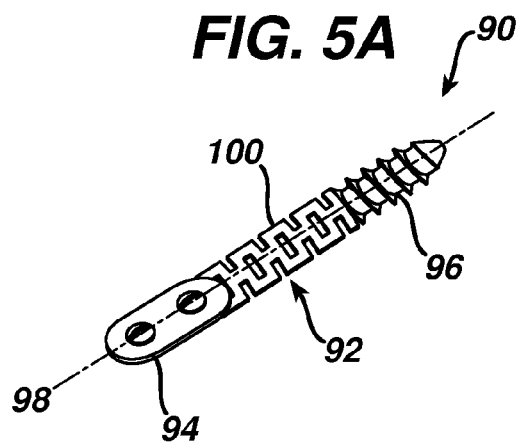
FIG. 5A is a perspective view of another embodiment of a vertebral implant having an elongate body with a deformable portion for increasing the size of a spinal canal of a vertebra, the deformable portion being in an unexpanded configuration.
Figure 5B:
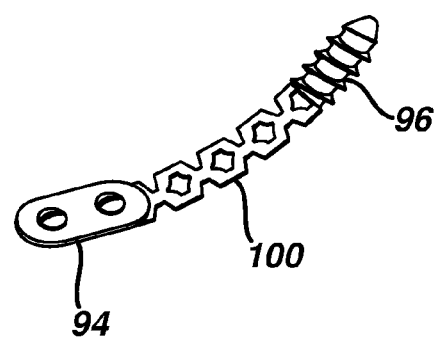
FIG. 5B is a perspective view of the vertebral implant of FIG. 5A with the deformable portion being in an expanded configuration for increasing the size of a spinal canal of a vertebra.
Figure 5C:
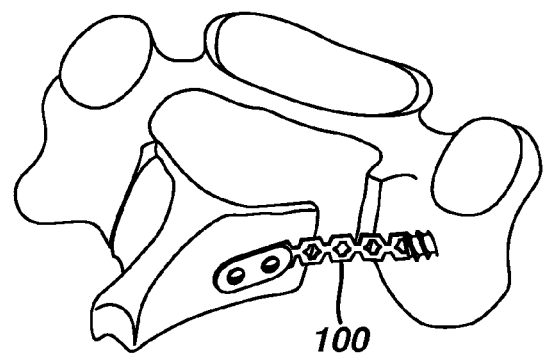
FIG. 5C is a perspective view of a vertebra having the vertebral implant of FIG. 5A coupled to first and second locations thereon showing the deformable portion of the implant expanded to increase the size of a spinal canal of the vertebra.

In yet another exemplary embodiment, shown in FIGS. 5A-5C, a vertebral implant 90 is provided that generally has an elongate configuration with a first end 94 configured to be coupled to a first location on a vertebra, and a second end 96 configured to be coupled to a second location on a vertebra. A deformable portion 92 is formed between the first and second ends 94, 96 and it is in the form of a mesh tube 100 that is configured to be stretched in the expanded configuration, as shown in FIGS. 5B-5C, to an increased length to increase the size of the spinal canal of the vertebra. For example, the deformable portion 92 can expand in an inferior and/or medial direction. The deformable portion 92 can have a curvature, shown in FIG. 5B, such that the deformable portion 92 is curved away from the bone between the first and second ends 94, 96. In use, the deformable portion 92 allows a tool to be passed through or adjacent to the deformable portion 92 so the bone positioned and extending between the first and second ends 94, 96 can be cut without interference from the deformable portion 12. In particular, the curvature in the deformable portion 92 exposes the bone, thus providing access to the bone.

Figure 6A:
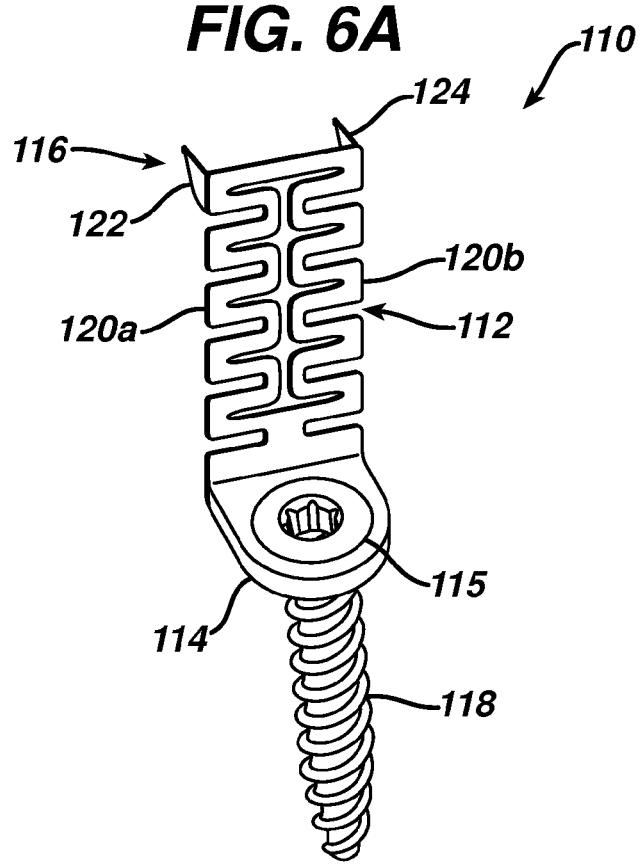
FIG. 6A is a perspective view of another embodiment of a vertebral implant having an elongate body with a deformable portion for increasing the size of a spinal canal of a vertebra.
Figure 6B:
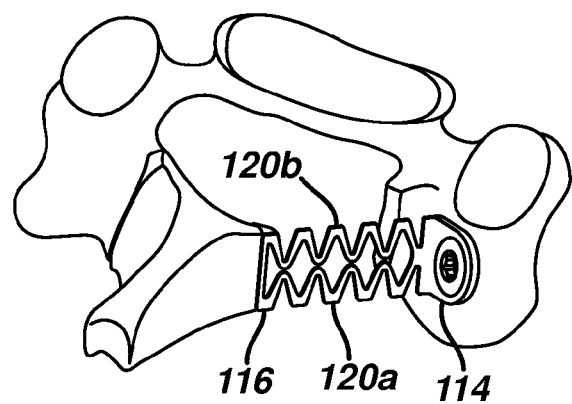
FIG. 6B is a perspective view of a vertebra having the vertebral implant of FIG. 6A coupled to first and second locations thereon showing the deformable portion of the implant expanded to increase the size of a spinal canal of the vertebra.

In yet another exemplary embodiment, shown in FIGS. 6A-6B, a vertebral implant 110 is provided that has an elongate configuration with a first end 114 configured to coupled to a first location on a vertebra, and a second end 116 configured to coupled to a second location on a vertebra. A deformable portion 112 is formed between the first and second ends 114, 116 and it is in the form of an elongate plate having first and second expandable members, each having a plurality of cut-outs 120a, 120b formed therein, similar to the embodiment shown in FIG. 4 and described above. The first and second members are coupled at each end such that the entire structure can be stretched into the expanded configuration to increase the size of a spinal canal of the vertebra. In use, the cut-outs 120a, 120b allow a tool to be passed through the deformable portion 112 so the bone positioned and extending between the first and second ends 114, 116 can be cut without interference from the deformable portion 112. For example, the tool can be passed through any of the cut-outs 120a, 120b to allow the tool to cut bone, or the deformable portion 112 can be deformed out of the way of the tool during cutting The various embodiments of the deformable portions described above can have a variety of shapes and sizes to increase the size of a spinal canal. For example, while the length of the deformable portion 12 can vary, the deformable portion 12 preferably has a length, as measured between the first and second ends 14, 16 when fully expanded into a linear configuration, that is sufficient to increase a distance between the first and second locations on the vertebra when the deformable portion 12 is in the expanded configuration so as to increase the size of the spinal canal as needed. For example, the length can be in the range of about 7 to 20 mm. The deformable portion 12 can also have various thicknesses, but the deformable portion 12 preferably has a thickness that facilitates the ability of the deformable portion 12 to maintain the distance between the first and second locations on the vertebra when the deformable portion 12 is in the expanded configuration.

The first and second ends 14, 16 can also have a variety of configurations to facilitate coupling to the first and second locations on a vertebra. In the embodiment shown in FIGS. 1A-1C, the first and second ends 14, 16 have a plate-like configuration with an ovular shape that defines a long axis extending therethrough. A person skilled in the art will appreciate, however, that the first and second ends 14, 16 can have any shape to facilitate mating to bone. The first and second ends 14, 16, can be oriented in a variety of ways to accommodate the bone of the vertebra. In the illustrated embodiment, the first end 14 can have a long axis 15 that is aligned or substantially parallel to the axis A, and the second end 16 can have a long axis 17 that can be oriented substantially perpendicular to the axis A. This can be advantageous as the first end 14 can be coupled to narrower bone located adjacent to the spinous process, and aligning the first end 14 with the axis A can accommodate the narrow bone. The second end 16 can be coupled to wider bone near the pedicles, thus allowing the second end 16 to be oriented perpendicular to axis A. A person skilled in the art will appreciate, however, that the first and second ends 14, 16 can be coupled to the first and second locations on the vertebra in any orientation or can have any shape that accommodates the bone of the first and second locations.

The first and second ends 14, 16 can be coupled to the deformable portion 12 in a variety of ways, including being unitary with the deformable portion 12 or as separate components that can be coupled to the deformable portion 12 using any technique known in the art. The first and second ends shown in FIGS. 2A-4 can have similar configurations to first and second ends 14, 16 shown in FIGS. 1A-1C.

The first end and second ends 14, 16 can also be coupled to bone in a variety of ways. In an exemplary embodiment, the first and second ends 14, 16 can include one or more thru-holes formed therethrough for receiving fasteners 18 to mate the first and second ends 14, 16 to bone. In the embodiment of FIGS. 1A-1C, each of the first and second ends 14, 16 includes first and second thru-holes extending therethrough and configured to receive a fastener 18 to couple the first and second ends 14, 16 to bone. The illustrated bores are positioned along the long axis. The fasteners 18 can have a variety of configurations, but in the illustrated embodiment they are each in the form a screw configured to be inserted into the thru-hole and into bone. A person skilled in the art will appreciate that the fasteners 18 can have any configuration that facilitates coupling to the first and second locations on the vertebra. The fasteners 18 can be located anywhere on the first and second ends 14, 16, but in the illustrated embodiment, first and second fasteners 18a, 18b on the first end 14 are located along the long axis 15 of the first end 14, and first and second fasteners 18c, 18d on the second ends 16 are located along the long axis 17 of the second end 16. A person skilled in the art will appreciate, however, that any number of fasteners 18 can be located in any configuration on the first and second ends 14, 16.

Various other configurations can be used to couple the first and second ends to bone. For example, in the embodiment shown in FIGS. 5A-5C, the first end 94 has an elongate plate-like configuration similar to the one described above with respect to FIGS. 1A-1C. The second end 96 has an elongate threaded member disposed therethrough or formed thereon and configured to be implanted into bone. The threaded member can extend in the same direction as an axis 98 of the deformable portion 92, and it can be integrally formed with the second end 96 or it can be rotatable relative to the second end 96, for example, by being disposed within a thru-bore formed in the second end 96. In another embodiment, shown in FIGS. 6A-6B, the first end 114 is in the form of an elongate plate that extends in a plane that is substantially perpendicular to a plane containing the deformable portion 112. The first end 114 includes a thru-hole formed 115 therein that is configured to receive a fastener 118 therethrough for mating to bone. The fastener 118 can have a variety of configurations, but in the illustrated embodiment it is in the form of a threaded screw. While the first end 114 includes a single thru-hole 115 for receiving a single fastener 118, a person skilled in the art will appreciate that the first end 114 can include any number of thru-holes and fasteners as necessary for mating to bone. The second end 116 is in the form of a clamp for engaging bone. The clamp can have various configuration, but in the illustrated embodiment it includes first and second projections or spikes 122, 124 extending from the second end 114 of the elongate body 112 in a direction that is substantially perpendicular to a plane containing the deformable portion 112. The first and second projections 122, 124 are configured to extend into or around bone to engage bone therebetween.

A person skilled in the art will appreciate that any of the configurations of the first and second ends of implant described above can be used with any of the illustrated embodiments shown in FIGS. 1A-6. Moreover, a person skilled in the art will also appreciate that the first and second ends can have any configuration that facilitates coupling to the first and second locations on the vertebra. In addition, a person skilled in the art will appreciate that both the first and second ends can be coupled to bone and then a cut can be formed therebetween, or one of the first and second ends can be coupled to bone, the bone can be cut, and then the other of the first and second ends can be coupled to bone.

The first and second ends can also include various features to facilitate movement of the deformable portion between the unexpanded and expanded configurations. For example, in the embodiment shown in FIGS. 1A-1C, the first and second ends 14, 16 can include first and second notches 22, 24 that are configured to receive a tool for pushing the first and second ends 14, 16 apart to increase the size of the spinal canal of the vertebra. The notches 22, 24 can have a variety of configurations, but in the illustrated embodiment, the notches 22, 24 are in the form of semi-circular cut-out portions formed in the first and second ends 14, 16. A person skilled in the art will appreciate, however, that the first and second notches 22, 24 can have any size and shape that can removably couple with any type of tool or instrument that can push the first and second ends 14, 16 apart. A person skilled in the art will also appreciate that any of the first and second ends shown in FIGS. 2A-6B can include notches, such as first and second notches 42, 44 shown in FIGS. 2A-2B, for pushing the first and second ends apart. Moreover, any type of member that can removably couple to a tool for pushing the first and second ends apart can be used, such as a protrusion, a button, or any other component known in the art. The notches 42, 44 can be positioned in a variety of ways on the first and second ends 14, 16, but in the illustrated embodiment they are positioned adjacent to the intersection between the deformable portion 12 and the first and second ends 14, 16. The notches 42, 44 can also be positioned such that the notches 42, 44 are facing one another, i.e., that the semi-circular cut-outs forming the notches 42, 44 are mirror-images of one another, such that a tool can be positioned in the notches 42, 44 to move the deformable portion 12 into the expanded configuration.

Figure 7:
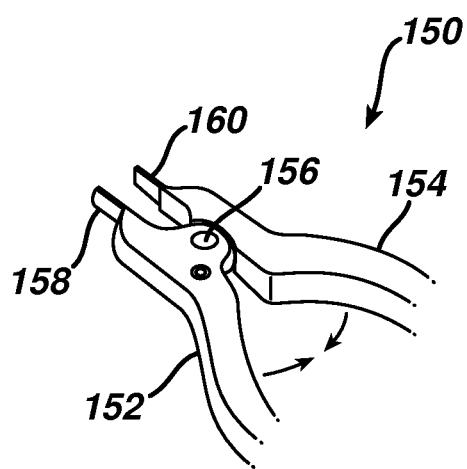
FIG. 7 is a perspective view of a tool for use with a vertebral implant for expanding a deformable portion of the implant for increasing the size of a spinal canal of a vertebra.

Various tools or instruments can be used to expand the deformable portion in any of the embodiments described above from the unexpanded configuration to the expanded configuration to increase the size of a spinal canal of a vertebra. In one exemplary embodiment shown in FIG. 7, a device 150 includes first and second elongate arms 152, 154 that are coupled to one another at a pivot point 156. The first and second elongate arms 152, 154 include first and second opposed jaws 158, 160 formed on distal ends thereof that are configured to engage the implant. For example, the opposed jaws 158, 160 can be sized and shaped to be received by the first and second notches 22, 24 shown in FIGS. 1A-1C to push the first and second ends apart. When proximal ends of the first and second elongate arms 152, 154 are moved together, the first and second opposed jaws 158, 160 will open. In use, the opposed jaws 158, 160 can be positioned in the notches 42, 44 such that the first and second ends 14, 16 abut an outer portion of each jaw 158, 160. The proximal ends of the first and second elongate arms 152, 154 are then squeezed to open the opposed jaws 158, 160 to expand the deformable portion into the expanded configuration. A person skilled in the art will appreciate that various other type of devices can be used to expand the deformable portion. For example, the jaws 158, 160 can removably mate to first and second ends of an implant such that opening of the jaws 158, 160 will pull, rather than push, the deformable portion into the expanded configuration.

Other exemplary embodiments of devices for increasing the size of a spinal canal are disclosed in U.S. Publication No. 2010/0241230 filed on Mar. 18, 2009 and entitled "Laminoplasty Methods And Devices," which is hereby incorporated by reference in its entirety. A person skilled in the art will appreciate that any of the various embodiments disclosed in the aforementioned application can be used in any combination with the present invention.

When increasing the size of the spinal canal by increasing the distance between first and second locations on one lateral side of a vertebra, it can be advantageous to create a hinge in the other lateral side of the vertebra. The present invention thus provides for various embodiments of vertebral implants that are configured to create a hinge in a vertebra, as shown in FIGS. 8A-10C. In general, an implant is provided that includes a breakage point. The implant can be inserted through a portion of a vertebra, such as a lamina, such that the implant extends along an axis of the lamina that extends between the spinous process and the pedicles of the vertebra. The breakage point of the implant can be used to create a hinge at a predetermined location along the lamina.

Figure 8A:
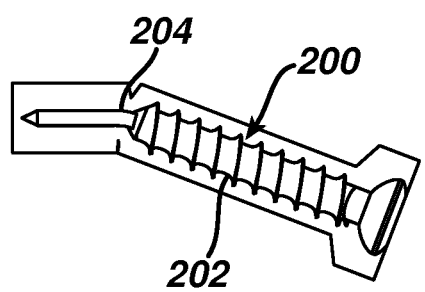
FIG. 8A is a cross-section of a portion of a vertebra having an elongate member implanted therein, the elongate member including a breakage point that is configured to form a hinge in the vertebra.
Figure 8B:
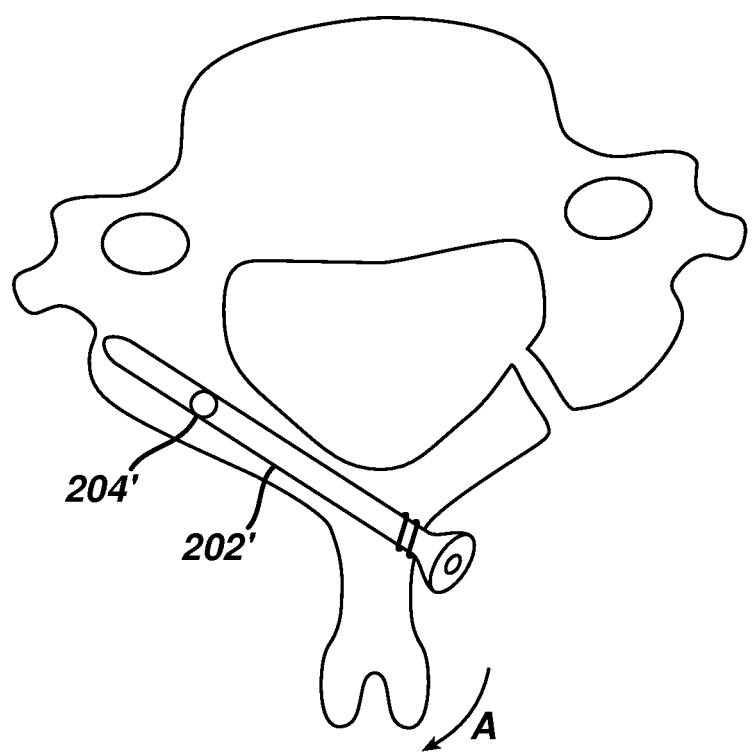
FIG. 8B is a top view of a vertebra having another embodiment of an elongate member implanted therein for forming a hinge in the vertebra.
Figure 8C:
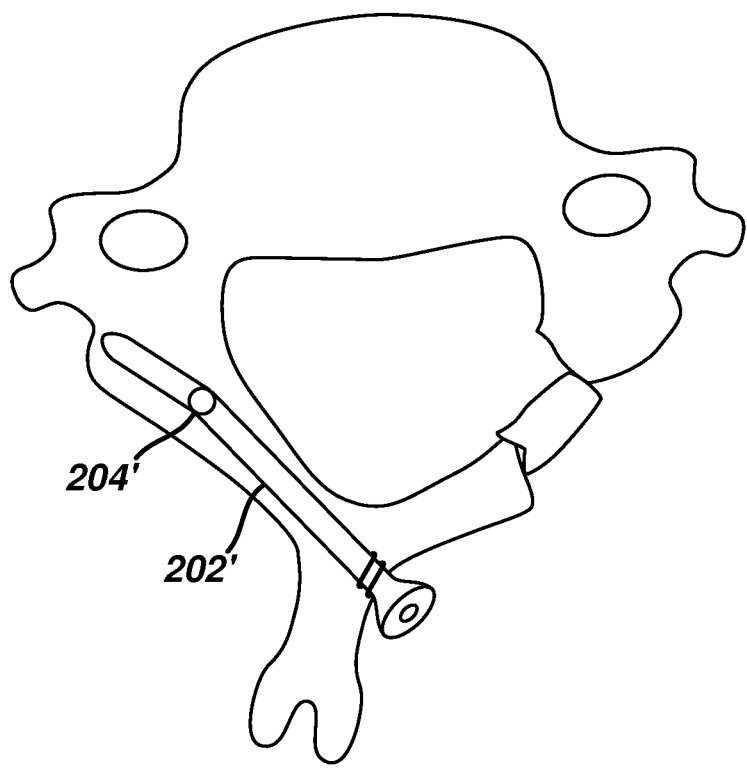
FIG. 8C is a top view of the vertebra and elongate member of FIG. 8B showing the elongate member forming a hinge in the vertebra.

In one exemplary embodiment shown in FIGS. 8A-8C, a vertebral implant 200 is provided for increasing the size of a spinal canal by creating a hinge in a vertebra. The implant 200 generally includes an elongate member 202 having a breakage point 204 located along a length thereof that is configured to form a hinge in a first lateral side of a vertebra. The breakage point is a location at which the implant causes the bone to be at least partially broken to create a hinge that allows the bone to pivot. The elongate member 202 can have a variety of configurations, but in the illustrated embodiment the elongate member 202 is generally in the form of an elongate shaft. While the length of the elongate member 202 can vary, the elongate member 202 preferably has a length that is sufficient to extend into a bore formed in the thin bone that extends between the spinous process and the pedicle on a first lateral side of the vertebra such that the breakage point 204 formed on the elongate member 202 is positioned at a location on the first lateral side where the hinge is desired. For example, the length can be in the range of 15 to 25 mm. The elongate member 202 can have a substantially smooth surface along its length as shown in FIGS. 8B-8C, or the elongate member 202 can include threads or other surface features formed thereon, as illustrated in FIG. 8A. The threads can be formed along the entire length of the elongate member 202 or can extend along any portion of the its length. For example, the threads can extend along the length of the elongate member 202 from its proximal end to a position just proximal of the breakage point 204, as shown in FIG. 8A. The proximal end of the elongate member 202 can include a head formed thereon, and the breakage point 204 can be located at a distal portion of the elongate member 202. While the breakage point 204 is shown positioned in the distal portion of the elongate member 202, the breakage point 204 can be positioned at any location along the length of the elongate member 202 depending on the desired location of the hinge in the first lateral side of the vertebra.

The breakage point 204 can have a variety of configurations in order to form a break in a lateral side of the vertebra to form a hinge. In the illustrated embodiment shown in FIG. 8A, the breakage point 204 is in the form of a flexible region formed in the elongate member 202. The breakage point 204 can be formed from a variety of materials that allow that portion of the elongate member 202 to flex to form the hinge, including but not limited to any elastomeric materials known in the art. In another embodiment illustrated in FIGS. 8B-8B, the breakage point 204' is in the form of a hinge or pivot joint formed in the elongate member 202'. The proximal end of the elongate member 202' can be moved in the direction of arrow A shown in FIG. 8B in order to form a hinge in the lateral side of the vertebra, as shown in FIG. 8C. In another embodiment, the breakage point can also be the distal end of the elongate member 202 such that the break in a lateral side of the vertebra is formed at the location of the distal end of the elongate member 202.

Figure 9:
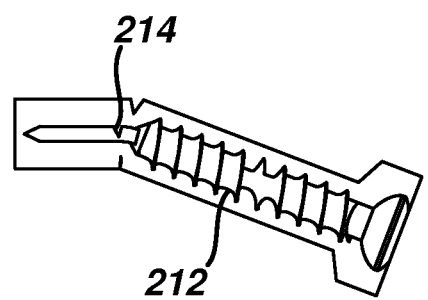
FIG. 9 is a cross-section of a portion of a vertebra having another embodiment of an elongate member implanted therein, the elongate member including a breakage point that is configured to form a hinge in the vertebra.

In another exemplary embodiment, shown in FIG. 9, a breakage point formed along an elongate member 212 is in the form of a weakened region formed on the elongate member 212 that is configured to break and form the hinge in the first lateral side of the vertebra. The weakened region can have a variety of configurations, including but not limited to being formed from a weaker material than the other portions of the elongate member 212, or it can be in the form of a surface feature, such as a notch 214 shown in FIG. 9, formed on the elongate member 212 that is configured to break when pressure is applied thereto. The weakened region can extend along a portion of the distal end of the elongate member 212, or can preferably be a single point along the elongate member 212 to ensure the location of the break formed in the first lateral side of the vertebra.

Figure 10A:
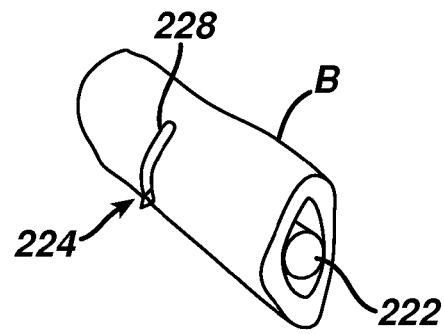
FIG. 10A is a perspective cross-section of vertebra having another embodiment of an elongate member implanted therein, the elongate member including a probe that is configured to form a hinge in the vertebra.
Figure 10B:
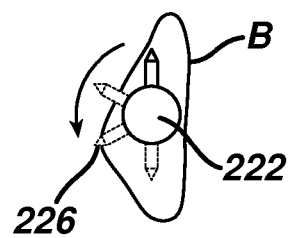
FIG. 10B is a cross-section of the vertebra having the elongate member of FIG. 10A implanted therein showing the probe being moved to protrude from the elongate member.
Figure 10C:
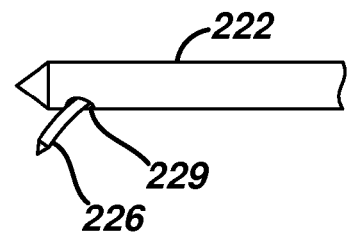
FIG. 10C is a side view of the elongate member of FIG. 10A with the probe protruding therefrom.

In yet another exemplary embodiment, shown in FIGS. 10A-10C, the breakage point 224 is in the form of a probe 226 that is removably disposable within the elongate member 222 and movable between a first position in which a distal end of the probe 226 is disposed within the elongate member 222, and a second position in which the distal end of the probe 226 protrudes from an opening 229 formed in a sidewall of the elongate member 222 to penetrate bone and cause the first lateral side to break and form a hinge. The elongate member 222 can be cannulated to allow the probe 226 to be inserted therein. The probe 226 can have a variety of configurations, but in the embodiment of FIGS. 10A-10C, which illustrates the elongate member 222 inserted into bone B, the probe 226 is in the form of an elongate cylindrical component with a pointed distal end that can protrude through an opening in a sidewall of the elongate member 222 and that is configured to penetrate bone and form a break therein. While the length of the probe 226 can vary, the probe 226 has a length that allows it to be inserted into the elongate member 222 such that a distal end of the probe 226 can protrude from the elongate member 222 enough to penetrate bone to form the hinge. A proximal end of the probe 226 can extend from the elongate member 222 and be held by a user, or it can be removably locked to the elongate member 222 so that the elongate member 222 and the probe 226 can rotate together. The probe 226 can be moved between the first and second positions by moving the probe 226 distally to cause the distal end of the probe 226 to protrude from an opening formed in the elongate member 222. The opening formed in the elongate member can have a variety of sizes and shapes in order to accommodate the probe 226. For example, in the illustrated embodiment of FIGS. 10A-10C, the opening 229 is in the form of a thru-hole formed in the wall of the elongate member 222 and has a size and shape such that the probe 226 can slide through the thru-hole and protrude from the elongate member 222. The opening 229 can be formed in any location along the length of the elongate member 222, but in the illustrated embodiment the opening 229 is formed in a distal end portion of the elongate member 222. A person skilled in the art will appreciate, however, that the opening 229 can have any configuration that allows a probe to be pushed therethrough and protrude from the elongate member. The probe 226 can penetrate bone as it protrudes from the elongate member 222. The elongate member 222 and the probe 226 can then form a break in the bone in a variety of ways. In one embodiment, the elongate member 222 with the probe 226 protruding therefrom can be rotated to form a slit 228 in the bone. In another embodiment, the probe 226 can protrude from the elongate member 222 to penetrate bone and then be moved proximally such that the probe 226 is retracted back inside the elongate member 222. The elongate member 222 can then be rotated such that the probe 226 can protrude from the elongate member 222 and penetrate the bone at a different location. This can be repeated any number of times to allow the probe 226 to penetrate the bone in a number of locations such that a perforation or slit is formed in the bone that can allow for bending or breaking of the bone. A person skilled in the art will appreciate that the probe can have a variety of other configurations. For example, the probe can be slidably coupled to an inner surface of the elongate member 222, and a tool can be inserted into the elongate member 222 to cause the probe 226 to protrude from the opening 229.

The present invention also provides a laminoplasty implant kit that includes one or more of the implants shown in FIGS. 8A-10C for forming a hinge in a first lateral side of a vertebra, and one or more of the vertebral implants shown in FIGS. 1A-6 for coupling to a second lateral side of the vertebra for increasing the distance between first and second cut locations on the second lateral side of the vertebra to increase the size of a spinal canal of the vertebra. A person skilled in the art will appreciate that any of the implants described above can be used in any combination to form the implant kit.

Figure 11A:
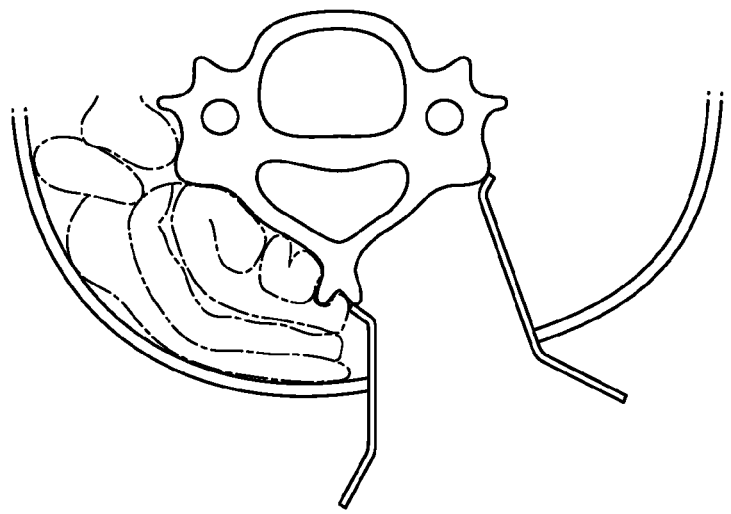
FIG. 11A is a top view of a vertebra showing an access port extending from a tissue surface to the vertebra for implanting vertebral implants for increasing the size of a spinal canal of the vertebra.
Figure 11B:
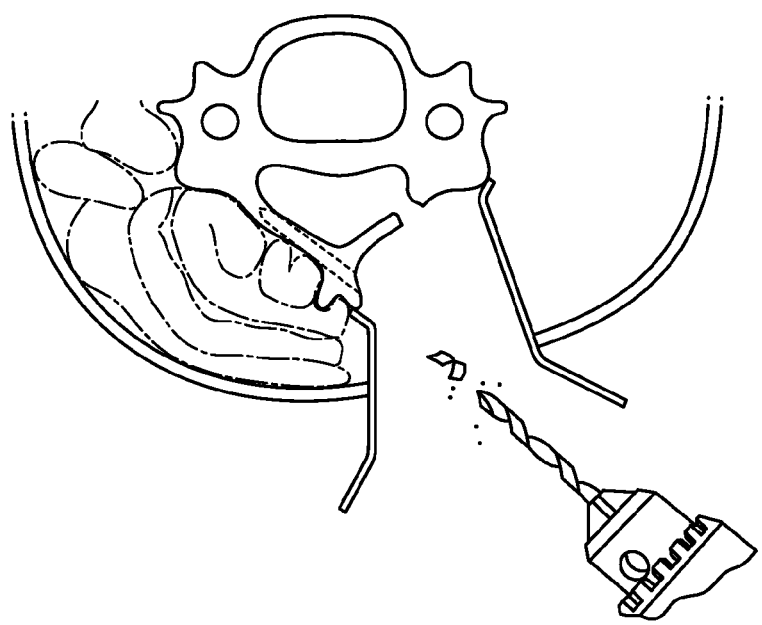
FIG. 11B is a top view of the vertebra and access port of FIG. 11A showing a tool extending through the access port to form an opening in the vertebra for establishing a breaking point and/or receiving an elongate member having a breakage point to form a hinge in the vertebra.
Figure 11C:
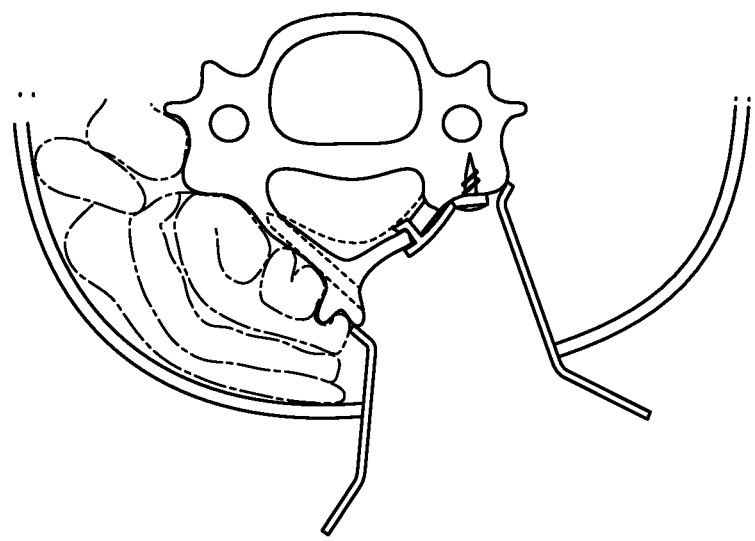
FIG. 11C is a top view of the vertebra and access port of FIG. 11A having an implant coupled thereto that increases the size of a spinal canal of the vertebra.

The present invention also provides methods for increasing the size of the spinal canal, as illustrated in FIGS. 11A-11C. An access port can be formed through tissue to expose a portion of a vertebra, for example, a second lateral side of the vertebra, for implantation of the devices for increasing the size of the spinal canal. A hinge can be formed in a first lateral side of a vertebra in the bone between the spinous process and the pedicles of the vertebra, for example, by accessing the first lateral side of the vertebra through the access port and forming a cut in the first lateral side of the vertebra, or by using an elongate member as described above. In one exemplary embodiment, an elongate member having a breakage point along its length can be implanted into a bore that is preformed in a first lateral side of a vertebra using, for example, a drill such as the one shown in FIG. 11B, or the elongate member can be self-drilling such that it forms the bore in the vertebra as it is implanted therein. The bore can extend along an axis of the first lateral side of the vertebra that extends between the spinous process and the pedicle. The elongate body is positioned within the bore in the first lateral side of the vertebra such that the breakage point is positioned at the desired location of a hinge to be formed in the first lateral side of the vertebra. In another exemplary embodiment, the hinge can be formed in the first lateral side of the vertebra without the use of the elongate member. The bore formed in the first lateral side of the vertebra can create a stress concentration point at the distal end of the bore, which can allow for bending and/or breaking of bone at the distal end of the bore. A variety of other techniques can be used to weaken the bone at the distal end of the bore to allow for bending and/or breaking of bone without the need for the elongate member. For example, mechanical techniques, including vibration or ultrasonics, can be used, or thermal techniques, including a heat probe, laser tip, or electrocautery device inserted into the bore can be used. Chemical techniques can also be used, such as applying a bone softening agent, such as an acid or an enzyme, within the bore at a distal end thereof to dissolve the calcium matrix of the first lateral side of the vertebra.

On the second lateral side of the vertebra, first and second ends of an elongate body are coupled to the first and second locations on the second lateral side. A cut separating the first and second locations can be made on a portion of the vertebra, such as the lamina, before or after the first end and/or the second end are coupled thereto, but preferably the first and second ends of the elongate body are mated to the first and second locations on the vertebra before the cut is made. Alternatively, the cut can be made between the first and second locations and then the first and second ends can be coupled thereto. In order to increase the distance between the first and second locations, the deformable portion is deformed, e.g., using a tool, such as device 200, removably coupled to the deformable member, to expand the deformable portion into the expanded configuration by either pushing or pulling the deformable portion apart. As the deformable portion is deformed, the distance between the first and second ends of the elongate body increases. This increases the distance between the first and second locations on the vertebra as the first end is coupled to the first location and the second end is coupled to the second location. Thus, the first and second locations on the vertebra are forced apart. The break in the first lateral side can already have been formed or, at the same time as the first and second locations on the second lateral side of the vertebra are forced apart, the movement forcing them apart can cause the breakage point of the elongate member to form a break in the first lateral side of the vertebra, thus forming a hinge therein. The deformable portion is configured to maintain the distance between the first and second locations on the second lateral side to increase the size of the spinal canal of the vertebra.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for increasing a size of a spinal canal, comprising:
 coupling a first end of an implant to a first location on a vertebra;
 coupling a second end of the implant to a second location on the vertebra;

after coupling the first and the second ends of the implant to the vertebra such that a deformable portion of the implant extends between the first and second ends, cutting the vertebra between the first and second locations; and deforming the deformable portion of the implant to increase and maintain a distance between the first and second locations on the vertebra thereby increasing a size of a spinal canal extending through the vertebra.

2. The method of claim 1, wherein deforming the deformable portion of the implant comprises inserting a tool between the first and second ends of the implant, and actuating the tool to apply a force to the first and second ends of the implant to increase a distance therebetween.

3. The method of claim 2, wherein deforming the deformable portion of the implant stretches out at least one bend formed in the deformable portion.

4. The method of claim 1, wherein coupling at least one of the first and second ends of the implant to the first and second locations on the vertebra comprises inserting a fastener through a thru-hole formed in the implant and inserting the fastener into the vertebra.

5. The method of claim 1, wherein the first and second locations are on a lamina located on a first side of a spinous process of the vertebra, and wherein cutting the vertebra comprises separating the lamina into two portions.

6. The method of claim 5, further comprising forming a hinge in a lamina located on a second side of the spinous process of the vertebra.

7. The method of claim 1, wherein the deformable portion maintains a fixed distance between the first and second ends of the implant.

8. The method of claim 1, wherein when the deformable portion is in an undeformed configuration, the deformable portion is V-shaped.

9. A method for increasing a size of a spinal canal, comprising:

coupling a first end of an implant to a first location on a vertebra;

coupling a second end of the implant to a second location on the vertebra, the implant having a bend formed therein disposed between the first and second ends, the bend defining a first angle;

cutting the vertebra between the first and second locations;

inserting a spreading tool between the first and second ends of the implant, and actuating jaws of the spreading tool such that the jaws apply a force to the first and second ends of the implant that increases the angle of the bend, thereby increasing a distance between the first and second locations on the vertebra and increasing a size of a spinal canal extending through the vertebra.

10. The method of claim 9, wherein coupling the first and second ends of the implant to the first and second locations on the vertebra comprises inserting a fastener through a thru-hole formed in the implant and inserting the fastener into the vertebra.

11. The method of claim 9, wherein the first and second locations are on a lamina located on a first side of a spinous process of the vertebra, and wherein cutting the vertebra comprises separating the lamina into two portions.

12. The method of claim 9, wherein prior to actuating the jaws, the implant is in an unexpanded configuration in which the angle of the bend is 40 degrees or less.

13. The method of claim 12, wherein when the implant is in the expanded configuration, the deformable portion has a length in the range of about 7 to 20 mm.

14. The method of claim 9, wherein actuating the jaws moves the implant to an expanded configuration in which the deformable portion maintains a fixed distance between the first and second ends of the implant.

15. The method of claim 9, wherein prior to actuating the jaws, the implant is in an unexpanded configuration in which the bend is V-shaped.

* * * * *